United States Patent [19]

Van Dalen et al.

[11] Patent Number: 6,100,407
[45] Date of Patent: Aug. 8, 2000

[54] PROCESS FOR PRODUCING SIMVASTATIN AND/OR ITS DERIVATIVES

[75] Inventors: Frans Van Dalen, Nuenen; Jacohus Maria Lemmens, Mook; Gertruda Antonetta Philomina Van Helvoirt, Nijmengen; Theororus Hendricus Antonius Peters, Arnhem, all of Netherlands; Frantisek Picha, Brno, Czech Rep.

[73] Assignee: Sython, B.V., Nijmegen, Netherlands

[21] Appl. No.: 09/263,097

[22] Filed: Mar. 5, 1999

[30] Foreign Application Priority Data

Mar. 5, 1998 [NL] Netherlands ............. 1008502

[51] Int. Cl.[7] .................. C07D 309/30; C07C 69/013
[52] U.S. Cl. ............. 549/196; 549/292; 549/373; 560/196
[58] Field of Search .................. 549/196, 292, 549/373; 560/196

[56] References Cited

U.S. PATENT DOCUMENTS

| | | |
|---|---|---|
| 4,444,784 | 4/1984 | Hoffman et al. . |
| 4,582,915 | 4/1986 | Sleteinger et al. . |
| 4,820,850 | 4/1989 | Verhoeven et al. . |
| 5,393,893 | 2/1995 | Kubela et al. . |
| 5,763,646 | 6/1998 | Kumar et al. . |
| 5,763,653 | 6/1998 | Khanna et al. . |

FOREIGN PATENT DOCUMENTS

WO 98/32751  7/1998  WIPO .

OTHER PUBLICATIONS

Greene, T. W. "Protective Groups in Organic Synthesis" John Wiley & Sons New York, 1981.

*Primary Examiner*—Gary Geist
*Assistant Examiner*—Leigh C. Maier
*Attorney, Agent, or Firm*—Dickinson Wright PLLC

[57] ABSTRACT

A process for the production of simvastatin and its analogues that is efficient, economical and convenient involves the use of hydroxyl protected intermediates of formula (III) or (VII). These intermediates allow for direct alkylation of the butyrate side chain followed by deprotection and reformation of the lactone ring.

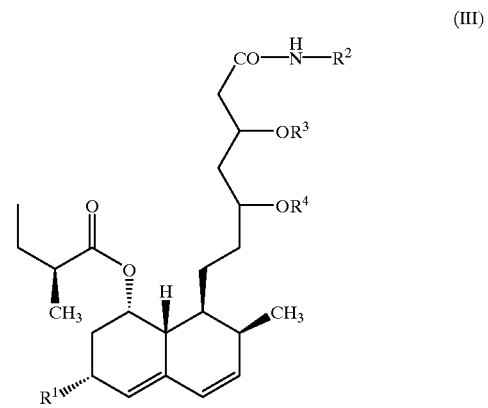

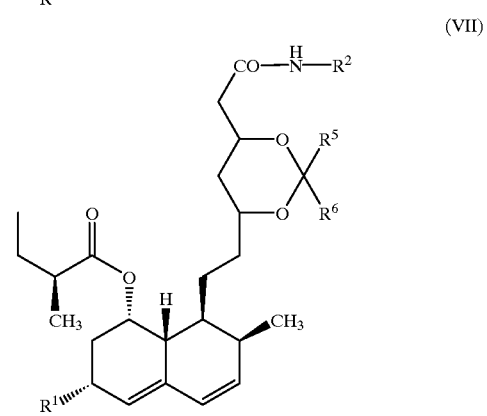

$R^1$ is hydrogen or methyl; $R^2$ represents a straight or branched chain alkyl group having 1 to 8 carbon atoms, a cycloalkyl group having 3 to 7 carbon atoms, or an aralkyl group having 1 to 6 carbon atoms in the alkyl chain; $R^3$ and $R^4$ each independently represent an alkyl group, an ether group, a thioether group, an aryl group, an aralkyl group, an alkenyl group, a cyclic ether group, or a cyclic thioether group; and $R^5$ and $R^6$ each independently represent hydrogen, an alkyl group, an aryl group, an aralkyl group, an alkoxy group, or an ether group.

19 Claims, No Drawings

PROCESS FOR PRODUCING SIMVASTATIN AND/OR ITS DERIVATIVES

The present invention relates to a process for producing simvastatin and/or derivatives thereof as well as to a process for producing intermediates for said compounds, and to various intermediates themselves.

BACKGROUND OF THE INVENTION

Certain hexahydronaphthalene derivatives are known as potent inhibitors of the enzyme HMG-CoA reductase, the rate-controlling enzyme in the biosynthetic pathway for formation of cholesterol in the human body. Well known examples of these compounds are mevastatin (U.S. Pat. No. 3,983,140), lovastatin (U.S. Pat. No. 4,231,938), pravastatin (U.S. Pat. No. 4,346,227) and simvastatin (U.S. Pat. No. 4,444,784). All of these compounds are important pharmaceuticals and are widely used in hyperchotesterolaemic treatments.

Mevastatin, lovastatin and pravastatin are natural fermentation products which possess a 2-methylbutyrate side chain in the 8-position of their hexahydronaphthalene ring system. It has been proven that products possessing a 2,2-dimethylbutyrate side chain in the same position (e.g. simvastatin (formula (A)) are even more active. Simvastatin is however, not naturally occurring.

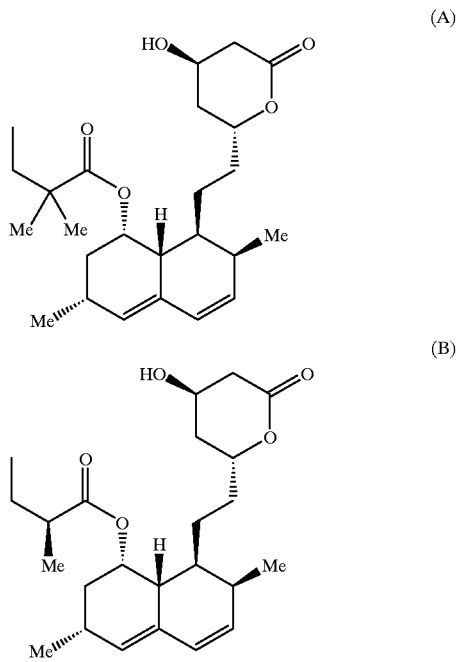

One route to introduce an additional α-methyl group to the 8-acyl side chain of lovastatin (formula (B)) or its analogues is disclosed in U.S. Pat. No. 4,444,784. This process involves indirect methylation of the said side chain through several chemical steps: deesterification of the whole 2-methylbutyrate side chain, protection of the 4-hydroxy group in the pyranone ring by a tert-butyldimethylsilyl protective group, reesterification of the protected lactone with 2,2-dimethylbutyric acid, and deprotection of the hydroxy group of the pyranone ring. This procedure involves multiple chemical reactions with a low overall yield.

Another route, based on direct methylation of the 8-acyl side chain of lovastatin and its analogues is disclosed in U.S. Pat. No. 4,582,915. Direct methylation of the 2-methylbutyrate side chain of lovastatin is achieved, after conversion to an alkali metal salt thereof, using a methylhalide in the presence of a strong base (metal alkylamide). Such a process exhibits disadvantages including low conversion, resulting in contamination of the product by a significant concentration of unconverted starting material and relatively high concentration of by-products.

The problems of low yields and poor quality of the final product have been addressed in a process disclosed in U.S. Pat. No. 4,820,850. This procedure comprises:

a) treatment of lovastatin with butylamine to achieve ring-opening of the lactone, followed by the protection of the hydroxyl-groups therein with tertbutyldimethylsilyl chloride;

b) treatment of the obtained protected intermediate with an alkalimetal amide followed by contact with alkylhalide to add an alkyl group to the 2-position of the butyrate side chain;

c) removal of the silyl protective groups by an acid, preferably hydrofluoric acid;

d) treatment with dilute base to hydrolyse the alkylamide; and e) heating of the resulting carboxylate salt in a hydrocarbon solvent to reform the lactone.

Another direct methylation process is described in U.S. Pat. No. 5,393,893. Here, a lovastatin-$C_3$–$C_7$-alkyl amide, cycloalkylamide or aralkylamide is prepared, the hydroxyl-groups thereof are protected with a phenylboronic acid and the resulting intermediate is further reacted with an alkyl-halide in the presence of a base to introduce the alkyl moiety into the butyrate side chain. The subsequent steps leading to simvastatin involve, similarly as in the preceding patent, the removal of the protective groups, hydrolysis of the alkylamide and relactonization to form simvastatin.

As apparent, the above synthetic routes, which involve the step of direct methylation, differ from each other namely by the nature of OH-protective groups in the reaction intermediates. These protected intermediates can be characterized by the presence of a C—O—Si— or C—O—B— linkage in their molecules.

However, in these known routes, the intermediates are quite unstable towards environmental hydrolysis and unstable towards strongly alkaline conditions during the methylation. As a result, undesirable amounts of by-products are formed during the synthesis. To obtain a product having the desired pharmaceutical quality, these by-products have to be removed by additional purification methods which lowers the overall yield and increases cost. Furthermore, the protecting agents used are economically undesirable.

SUMMARY OF THE INVENTION

The present invention relates to the use of ether-based hydroxyl protecting groups in the synthesis of simvastatin and its analogues. One embodiment of the invention is a process, which comprises reacting a compound of formula (II):

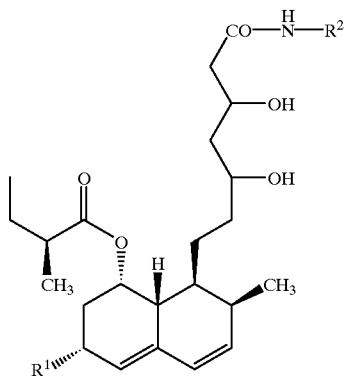

(II)

wherein R¹ represents hydrogen or methyl and R² represents a straight or branched chain alkyl group having 1 to 8 carbon atoms, a cycloalkyl group having 3 to 7 carbon atoms, or an aralkyl group having 1 to 6 carbon atoms in the alkyl chain;

with a protecting agent to form a compound of formula (III) or (VII):

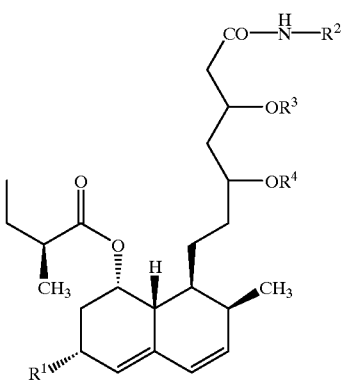

(III)

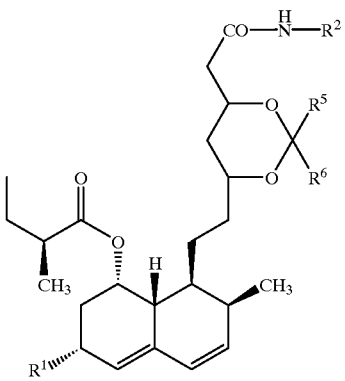

(VII)

wherein R¹ and R² are as defined above in formula (II), R³ and R⁴ each independently represents an alkyl group, an ether group, a thioether group, an aryl group, an aralkyl group, an alkenyl group, a cyclic ether group, or a cyclic thioether group, and R⁵ and R⁶ each independently represents hydrogen, an alkyl group, an aryl group, an aralkyl group, an alkoxy group, or an ether group.

The compounds of formula (III) and (VII) can be subjected to direct alkylation to produce compounds of formula (IV) and (VI), respectively.

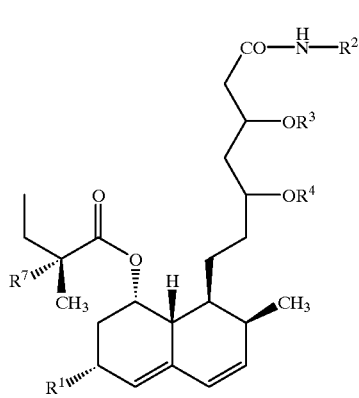

(IV)

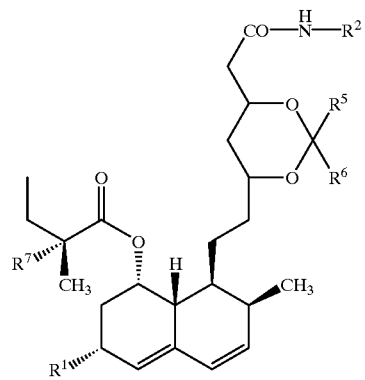

(VIII)

$R^7$ is methyl or ethyl and $R^3$–$R^6$ are as defined above. The compounds of formula (III), (IV), (VII), and (VIII) are a second embodiment of the invention.

A third embodiment of the invention is the subsequent production of simvastatin or its analogue by deprotecting the compound of formula (IV) or (VIII), hydrolyzing the alkylamide, and reforming the lactone ring to produce a compound of formula (VI).

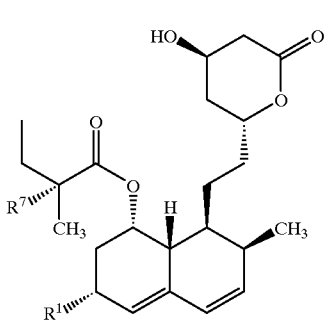

(VI)

By using a carbon terminated (i.e. ether-based) protecting group, the present invention can provide an economical, convenient and efficient process for making compounds of formula (VI) in high purity.

DETAILED DESCRIPTION OF THE INVENTION

The following reaction scheme summarizes various aspects and embodiments of the present invention.

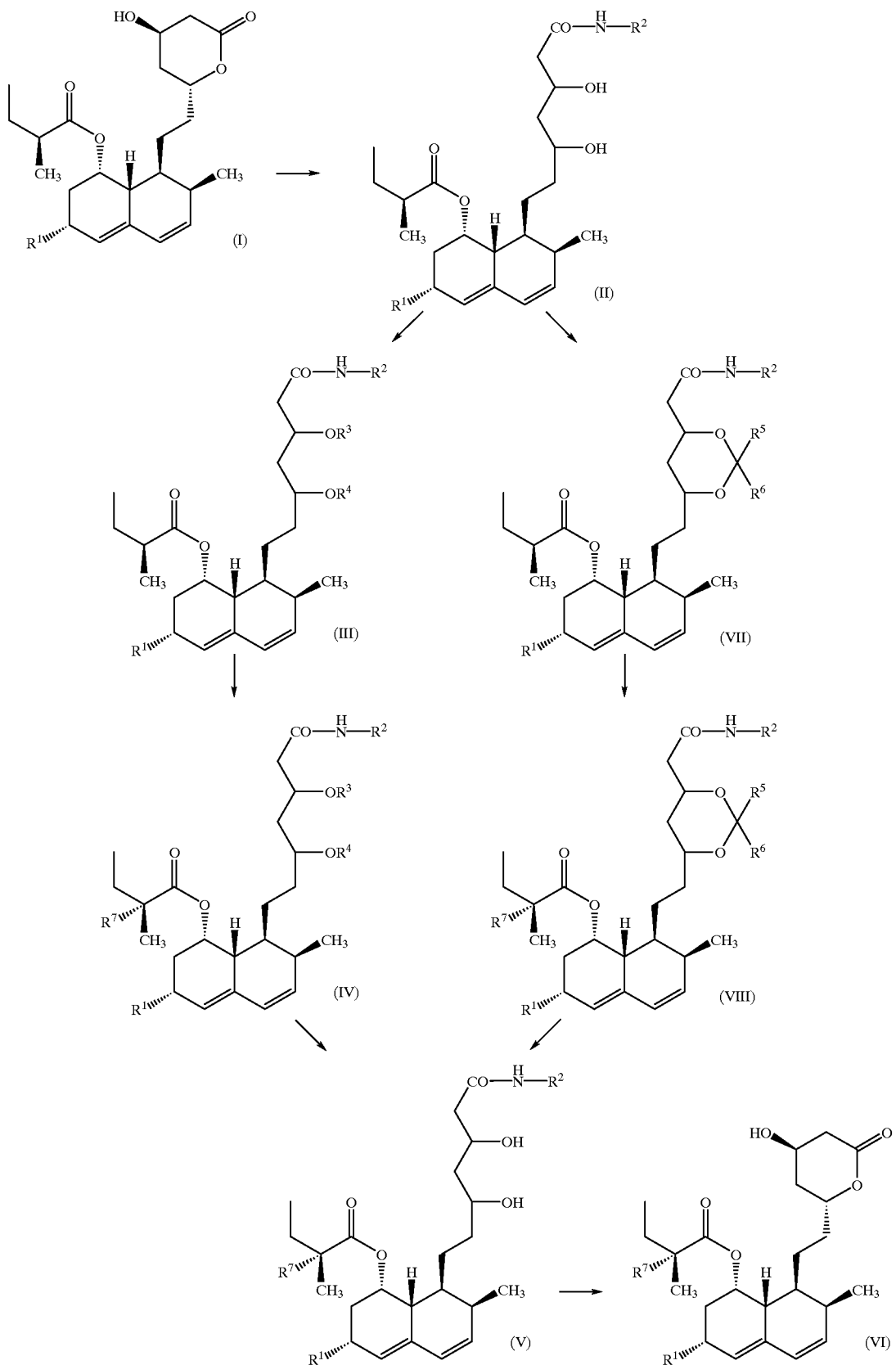

The compounds of formula (I) are known, naturally occurring compounds. $R^1$ is hydrogen or methyl. The compounds of formula (II) are formed by carrying out a ring opening reaction with an amine of the formula $R^2NH_2$. $R^2$ represents a straight or branched alkyl group of 1 to 8 carbon atoms, a cycloalkyl group of 3 to 7 carbon atoms, or an aralkyl group having 1 to 6 carbon atoms in the alkyl chain. Typically, the aralkyl group contains 1 to 4 carbon atoms in the alkyl moiety, although such is not required, and the aromatic moiety is phenyl or naphthyl. Examples of suitable $R^2$ groups include methyl, ethyl, propyl (iso- and n-forms), butyl (tert-, iso- and n-forms), cyclohexyl, cyclopentyl, benzyl, phenethyl, and 3-phenylpropyl.

When using a low boiling amine (such as methylamine or ethylamine) to form the alkylamide of formula (II), it is preferred that the reaction is carried out in an inert solvent, such as tetrahydrofuran or toluene. When employing high boiling amines (e.g. butylamine), the amine itself can be used as the solvent. After evaporation of the solvent and/or removal of the unreacted amine, the compound (II) is obtained. While the use of alkylamines having as few as three carbon atoms has been described in U.S. Pat. No. 4,820,850 and U.S. Pat. No. 5,393,893, the present invention further specifically contemplates the use of $C_1$ and $C_2$ amines (methylamine, ethylamine) in the amidation reaction as described above. This embodiment allows for easy purification of the product compound of formula (II) vis-a-vis the amine reactant in that any unused amine reactant can be readily volatized off. This provides a convenient and effective method to remove any excess amine impurity, especially if the compound of formula (II) is not isolated before the next reaction step.

The hydroxyl groups of the amide of formula (II) are then protected with carbon-terminated protective groups to form an ether as shown in formulas (III) and (VII). $R^3$ and $R^4$ independently represent an alkyl group, an ether group, a thioether group, an aryl group, an aralkyl group, an alkenyl group, a cyclic ether group, or a cyclic thioether group. The alkyl group generally contains 1 to 8 carbon atoms and can be straight or branched chain or cyclic (3–8 carbon atoms). The "ether group" means an acyclic chain having at least one C—O—C bond therein. Typically an ether group contains 2 to 8 carbon atoms and one or two oxygen linkages therein. The "thioether group" has the same meaning as the ether group except that the C—O—C linkage is replaced with the corresponding C—S—C linkage. An "aryl group" means a hydrocarbon aromatic radical such as phenyl. The "aralkyl group" means an aryl group having an alkyl linkage, typically a 1 to 4 carbon linkage. The "alkenyl group" means an unsaturated acyclic chain having 2 to 8 carbon atoms. The "cyclic ether group" means a 5 to 7, preferably 5 or 6, membered ring containing at least one ring oxygen. The ring can be saturated, unsaturated or aromatic. Preferred cyclic ethers are pyranyls, furanyls, and dioxanyls, including their partially and fully hydrated forms. The ring may be substituted by alkyl, alkoxy, or ether each having 1 to 4 carbons. Examples include tetrahydropyranyl, an alkoxytetrahydropyranyl, a dioxanyl, and tetrahydrofuranyl. Similarly, "cyclic thioether group" means a cyclic ether where the ring oxygen has been replaced by a ring sulfur; for example, a tetrahydrothiopyranyl. Specific examples of $R^3$ and $R^4$ groups are methyl, methoxymethyl, methylthiomethyl, benzyloxymethyl, t-butoxymethyl, 2-methoxyethoxymethyl, 1-ethoxyethyl, t-butyl, allyl, benzyl, tetrahydropyran-2-yl, tetrahydrothiopyran-2-yl, 4-methoxytetrahydropyran-2-yl, 1,4dioxan-2-yl or tetrahydrofuran-2-yl.

The $R^3$ and $R^4$ groups can be formed by reacting the amide of formula (II) with an appropriate donor of the carbon-terminated protective group by generally known methods. For example, by a substitution reaction with appropriate halogenides or sulphates of the protective group (e.g. alkyl, alkoxyalkyl, or benzyl halogenides, etc.) in the presence of a base, or by an addition reaction with an appropriate unsaturated compound (e.g. with 3,4-dihydro 2H-pyrane) in a suitable solvent, e.g. in dichloromethane, under catalysis by an acid (e.g. p-toluenesulfonic acid). Usually only one type of donor compound is used and thus $R^3$ and $R^4$ are usually identical to one another.

In formula (VII), $R^5$ and $R^6$ each independently represent hydrogen, an alkyl group, an aryl group, an aralkyl group, an alkoxy group, or an ether group. These groups have the same meaning as defined for $R^3$ and $R^4$ wherein the "alkoxy group" is an "alkyl group" linked by an oxygen atom to the ring carbon. Examples of $R^5$ and $R^6$ include hydrogen, lower alkyl (methyl, ethyl, propyl, butyl, etc.), phenyl, benzyl, methoxy, ethoxy or methoxymethyl.

The "cyclic ethers" of the formula (VII) can be made by reacting the amide of formula (II) with an appropriate donor of the carbon-terminated protective group by generally known methods. Typically, were at least one of groups $R^5$ and $R^6$ is hydrogen, the reaction uses a donor having an activated C=O group of the appropriate aldehyde (e.g. benzaldehyde). When neither $R^5$ nor $R^6$ is hydrogen, such as when both are alkyl, e.g. methyl, the compounds can be formed by reaction with an activated ketone. For example, acetone or its alpha substituted derivatives can be used in the presence of a strong acid (preferably p-toluenesulfonic acid) and a dehydrating agent (preferably silica gel, molecular sieves, sodium sulfate, or copper (II) sulfate), preferably at room temperature. Alternatively, 2,2-dimethoxypropane is another example of a donor compound that can be used in the presence of a strong acid (preferably p-toluenesulfonic acid), preferably at room temperature.

Thus, the "cyclic-ethers" of the formula (VII) can also be regarded as being cyclic acetals or ketals.

The reaction with a donor of the protective group according to the present invention generally proceeds with almost 100% conversion (e.g. 99.7% in case of acetonides) and under mild reaction conditions.

The following compounds of the formula (III) and (VII) are examples of useful compounds of the present invention:

lovastatin ethylamide bis-tetrahydropyran-2-ylether (compound (III), wherein $R^1$=methyl, $R^2$-ethyl, $R^3$=$R^4$=tetrahydropyran-2-yl)

lovastatin n-butylamide bis-tetrahydropyran-2-ylether (compound (III), wherein $R^1$=methyl, $R^2$=n-butyl, $R^3$=$R^4$=tetrahydropyran-2-yl)

lovastatin ethylamide acetonide (compound (VII) wherein $R^1$=methyl, $R^2$=ethyl, $R^5$=$R^6$=methyl)

lovastatin butylamide acetonide (compound (VII) wherein $R^1$=methyl, $R^2$=n-butyl, $R^5$=$R^6$=methyl).

Subsequently, the compounds of formula (IV) or (VIII) are prepared from compounds (III) or (VII) by alkylation. The alkylation of the protected amide (III) or (VII) can be carried out according to known methods, such as by adding an alkylating agent in the presence of a base. For example, the amide can be firstly treated with an alkali metal amide (which is prepared by known methods by a combination of n-butyllithium with a lower secondary amine, e.g. pyrrolidine or piperidine, in an etheral solvent, e.g. tetrahydrofuran) at a low temperature (−30° C. to −40° C.) and then the alkylating agent, normally of the general formula $R^7$-X, wherein $R^7$ represents methyl or ethyl and X represents a leaving group such as halogen (e.g. chlorine, bromine, iodine) or sulfate (e.g. mesylate, tosylate, etc.), can be added, preferably at the same temperature. Typically, the alkylating agent is an alkylhalide such as methyliodide. The alkylation reaction is preferably performed in inert atmosphere, e.g. under nitrogen. The reaction mixture can then be treated with cold water and the desired compound (IV) of (VIII) isolated. If the desired product is an oil, it can be isolated by extraction into an organic solvent, preferably ethyl acetate, followed by evaporation of the said solvent. If it is a solid, it can be isolated in the solid state after extraction and evaporation steps, namely by trituration of the residue after evaporation with an appropriate solvent in which the product is not soluble, e.g. in hexane.

The following compounds of the formula (IV) and (VIII) are examples of the compounds of the present invention:

Simvastatin ethylamide bis-tetrahydropyran-2-ylether (compound (IV), wherein $R^1$=methyl, $R^2$=ethyl, $R^3=R^4$=tetrahydropyran-2-yl, $R^7$=methyl)

Simvastatin n-butylamide bis-tetrahydropyran-2-ylether (compound (IV), wherein $R^1$=methyl, $R^2$=n-butyl, $R^3=R^4$=tetrahydropyran-2-yl, $R^7$=methyl)

Simvastatin ethylamide acetonide (compound (VIII) wherein $R^1$=methyl, $R^2$=ethyl, $R^5=R^6=R^7$=methyl)

Simvastatin butylamide acetonide (compound (VIII) wherein $R^1$=methyl, $R^2$=n-butyl, $R^5=R^6=R^7$=methyl).

The next step achieves deprotection of the hydroxyl groups in compounds (IV) or (VIII) to form a compound of formula (V). For this purpose, the ether linkages in compounds (IV) or (VIII) are subjected to hydrolysis, preferably to acidic hydrolysis, preferably using an aqueous solution of a strong organic acid e.g. methane sulfonic acid in a mixture with water miscible alcohol, e.g. methanol. Deprotected alkylated amide (V) results both from the compound (IV) and from the compound (VIII).

Similarly, a strong acidic resin can also be used for the same purpose or specific known cleavage methods can be applied.

In the last step, hydrolysis of the amidic group in the compound (V) can be performed without need of its isolation, by preferably heating the reaction mixture with an excess of an aqueous solution of a strong inorganic base (e.g., sodium hydroxide) under continuous removal of the alcohol. The reaction mixture is extracted by a water immiscible solvent, e.g., ethyl acetate, the organic layer is evaporated and final lactonization to yield the compound (VI) is performed by conventional methods, i.e., by boiling the distillation rest with toluene under continuous removal of water.

In all the steps, the solutions of any intermediate may be purified by treatment of activated charcoal, silica gel, kieselguhr or other suitable materials; another suitable method of purification is crystallization from a proper solvent. Nevertheless, these purifications must be applied only for characterization purposes. Due to high conversion and low amount of side products, all the reaction steps of the present invention proceed in practical production substantially without the need of purification. All the reaction steps are preferably performed under nitrogen atmosphere.

This process involves OH-protected derivatives of lovastatin or mevastatin as reaction intermediates, said derivatives having good stability, being easily synthetizable and allows preparation of the desired compounds in good yield and having good purity, wherein the use of expensive and unstable reactants for protection of the hydroxyl groups is substantially obviated.

The compounds of the present invention are characterized by infra-red spectra, NMR spectra and mass spectra as exemplified in the examples, see later.

In some cases, two new centers of chirality (e.g., on the carbons 2' in tetrahydropyrane rings) are introduced, so that certain compounds of the present invention exist as a mixture of enantiomers. It cannot be excluded that a person skilled in the art may easily find a method of their resolution into optically pure isomers, if necessary.

The compounds of the present invention can exist in unsolvated as well as solvated forms, including hydrated forms. In general, the solvated forms are equivalent to the unsolvated forms for purpose of the invention.

Except where specifically defined to the contrary, the term alkyl includes both the straight chain, branched chain and/or cyclic chain species with the same number of carbon atoms.

The following examples illustrate the invention.

EXAMPLES

Example 1a

Preparation of lovastatin ethylamide: N-ethyl-7-[1(S), 2(S), 6(R), 7,8(S), 8a(R)-hexahydro-2,6-dimethyl-8-[[2(S)-methylbutanoyl]oxy]-1-naphthyl]-3(R), 5(R)-dihydroxyheptanamide, compound of formula (II) (wherein $R^1$ is methyl and $R^2$ is ethyl).

A mixture of lovastatin (5.0 g, 0.012 mol) and 2N solution of ethylamine in tetrahydrofuran (37 ml, 0.074 mol) was heated to gentle reflux at 70° C. for 10 hours. The solution was cooled to ambient temperature and ethyl acetate (100 ml) was added; the mixture was washed with 2N hydrochloric acid (3×50 ml). The combined aqueous layers were washed with ethyl acetate (100 ml) and the combined organic layers with water (2×100 ml). The organic layer was dried over sodium sulphate, filtered and evaporated at reduced pressure to give an orange oil.

NMR (CDCl$_3$, delta scale): 6.22 (NH), 5.98 ($C_4$,-H), 5.78 ($C_3$,-H), 5.51 ($C_5$-H), 5.41 ($C_8$,-H), 4.81 (OH), 4.21 ($C_3$-H), 3.79 ($C_5$-H and OH) and 3.29 ($C_1$,-H).

Mass spectrum: m/e 449 (M*) with major fragments at m/e 431, 347, 224, 198, 172 and 159.

Infra red spectrum (NaCl): principal peaks at wave numbers (cm$^{-1}$) 3200–3500 (OH and NH), 2900–3015 (C—H), 1753 (ester C=O), 1664 (amide C=O), 1559 (amide C=O), 1208 (ester C—O—C).

Example 1b

Preparation of lovastatin ethylamide bis-tetrahydropyran-2-yl ether: N-ethyl-7-[1(S), 2(S), 6(R), 7,8(S), 8a(R)=hexahydro-2,6-dimethyl-8-[[2(S)-methylbutanoyl]oxy]-1-naphthyl]-3(R), 5(R)-bis[(tetrahydropyranyl)oxy] heptanamide, compound of formula (III) wherein $R^1$ is methyl, $R^2$ is ethyl, $R^3$ and $R^4$ are tetrahydropyran-2-yl).

To a solution of lovastatin ethylamide of the Example 1a (1.1 g, 2.5 mmol) in dichloromethane (10 ml), 3,4-dihydro-2H-pyran (1.1 ml, 12.1 mmol) and 24 mg para-toluenesulfonic acid monohydrate (24 mg, 0.13 mmol) were added. The solution was stirred at 20°–15° C. for 1.5 hours. Then cyclohexane (20 ml) and 5% m/V aqueous sodium bicarbonate (20 ml) was added. The mixture was stirred vigorously and the layers were allowed to separate. The organic layer was washed successively with 5% m/V aqueous sodium bicarbonate (20 ml) and distilled water (20 ml). The organic layer was dried over sodium sulfate, filtered and evaporated to dryness under reduced pressure to obtain an orange coloured oil.

NMR (CDCl3, delta scale): 6.92, 6.77, 6.39, 6.22 (NH), 5.98 ($C_4$,-H), 5.79 ($C_3$,-H), 5.51 ($C_5$,-H), 5.35 ($C_8$,-H).

Mass spectrum: m/e 617 (M*) with major fragments at m/3 516, 449, 347, 198, 172, 159 and 85.

Infra red spectrum (NaCl): principal peaks at wave numbers ($cm^{-1}$) 3324 (NH), 2880–3025 (C—H), 1730 (ester C=O), 1660 (amide C=O), 1540 (amide C=O), 1190 (ester C OC).

Example 1c

Preparation of simvastatin ethyl amide bistetrahydropyran-2-yl ether: N-ethyl-7-[1(S), 2(S), 6(R), 7,8(S), 8a(R) -hexahydro-2,6-dimethyl-8-[[2,2-dimethylbutanoyl]oxy]-1-naphthyl]-3(R), 5(R)-bis [(tetrahydropyranyl)oxy]heptanamide, compound of formula (IV) (wherein $R^1$ is methyl, $R^2$ is ethyl, $R^3$ and $R^4$ are tetrahydropyran-2-yl and $R^7$ is methyl).

n-Butyllithium in hexane (26 ml, 0.041 mol) was added to a stirred solution of pyrrolidine (3.5 ml 0.042 mol) in anhydrous tetrahydrofuran (12 ml) at –20° C. under an inert atmosphere of nitrogen. The mixture was stirred at –20° C. for 30 minutes and then added dropwise to a stirred solution of lovastatin ethylamide tetrahydropyranyl ether of the Example 1b (11.0 g, 0.018 mol) in tetrahydrofuran (48 ml) precooled at –35° C., in such a rate as to keep the temperature between –30° C. and –35° C. (see Note) After completion of the addition the mixture was stirred at –35° C. for 2 hours. Then methyliodide (1.7 ml, 0.027 mol) was added in one portion. After an initial 15° C. exotherm, the solution was recooled to –30° C. and maintained for an additional 30 minutes. The mixture was then quenched by addition of water (80 ml) and the mixture was allowed to warm to ~5° C., while stirring. The phases were separated and the aqueous layer was extracted with ethyl acetate (2×50 ml).

The combined organic layers were extracted with 1N aqueous hydrochloric acid (100 ml). The resulting organic phase was concentrated at reduced pressure to obtain an orange coloured oil.

NMR ($CDCl_3$, delta scale): 6.92, 6.78, 6.42, 6.25 (NH), 5.98 ($C_4$,-H), 5.78 ($C_3$,-H), 5.49 ($C_5$,-H), 5.33 ($C_8$,-H).

Infra red spectrum (NaCl): principal peaks at wave numbers ($cm^{-1}$) 3338 (NH), 2865–3000 (C—H), 1716 (ester C=O), 1649 (amid C=O), 1540 (amid C=O), 1162 (ester C—OC).

Note: The addition order can also be reversed without any influence on the results.

Example 1d

Preparation of simvastatin, compound of the formula (VI) (wherein $R^1$ is methyl and $R^7$ is methyl).

Step i

Preparation for simvastatin ethylamide: N-ethyl-7-[1(S), 2(S), 6(R), 7,8, (S), 8a(R)-hexahydro-2,6-dimethyl-8-[[2,2-dimethylbutanoyl]oxy]-1-naphthyl]-3(R), 5(R)-dihydroxyheptanamide, compound of formula (V) wherein $R^1$ is methyl, $R^2$ is ethyl and $R^7$ is methyl).

Methanol (50 ml) was added to the crude simvastatin ethylamide bistetrahydropyran-2-yl ether of the Example 1c (11.2 g). Then water (4 ml) and methanesulfonic acid (125 μl) were added and the resulting solution was stirred for 6 hours at 30° C.

For characterization purpose, an aliquot was evaporated, dissolved in ethyl acetate and extracted with an aqueous solution of sodium bicarbonate, water, dried over sodium sulfate, filtrated and evaporated to dryness to obtain an orange coloured oil.

NMR (CDCl3, delta scale): 6.29 (NH), 5.98 ($C_4$, -H), 5.78 ($C_3$,-H), 5.49 ($C_5$,-H), 5.40 ($C_8$,-H), 4.86 (OH), 4.21 ($C_3$-H), 3.86 (OH), 3.79 ($C_5$-H), and 3.29 ($C_1$,-H).

Infra red spectrum (NaCl): principal peaks at wave numbers (cm-1) 3297–3608 (OH and NH), 2878–3040 (C—H, 1716 (ester C=O), 1635 (amid C=O).

Step ii

Preparation of Simvastatin

To the clear methanol solution from the preceded step there was added 2N NaOH aqueous solution (60 ml) and the solution was heated to reflux for 5 hours while distillate (70 ml) was collected at ambient pressure. This mixture was allowed to cool down to ambient temperature, diluted with water (15 ml0 and cooled to 10° C. while adjusting the pH to 3 with 5N HCl (35 ml).

Ethyl acetate (100 ml) was added and after agitation, the phases were allowed to settle and were separated. The aqueous layer was extracted with ethyl acetate (2×50 ml), the combined organic layers were dried over sodium sulfate, filtered and evaporated at reduced pressure.

Then toluene was added (60 ml) and the solution was allowed to reflux with continuous separation of water for 6 hours.

Evaporation of the toluene, crystallization from cyclohexane and recrystallization from methanol/water yielded analytically pure simvastatin.

Melting point: 131°–133° C.

$[\alpha]_D$ (5 mg/ml acetonitrile): +286°

NMR ($CDCl_3$, delta scale): 5.99 ($C_5$-H), 5.79 ($C_6$-H), 5.51 ($C_4$-H), 5.37 ($C_1$-H), 4.63 ($C_2$,-H) and 4.36 ($C_4$,-H).

Mass spectrum: m/e 418 (M$^+$) with major fragments at m/e 302, 284, 199, 173 and 159.

Infra red spectrum (KRr): principal peaks at wave numbers ($cm^{-1}$) 3545 (OH), 2850–3050 (C—H), 1715 (ester C=O), 1700 (amide C=O), 1275 (lactone C—O—C) and 1170 (ester C—O—C).

Examples 2 to 5

Following the procedure substantially as described in Examples 1a to 1d(i), the following compounds (II) to (V) were prepared:

| Example | formula | $R_1$ | $R_2$ | $R_3$=$R_4$ | $R_7$ |
|---|---|---|---|---|---|
| 2 | II | methyl | n-butyl | — | — |
| 3 | III | methyl | n-butyl | THP | — |
| 4 | IV | methyl | n-butyl | THP | methyl |
| 5 | V | methyl | n-butyl | — | methyl |

(THP = tetrahydropyran-2-yl)

Example 2

Example 2=N-butyl-7-[1(S), 2(S), 6(R), 7,8(S), 8a(R)-hexahydro-2,6-dimethyl-8-[[2(S)-methylbutanoyl]oxy]-1-naphthyl]-3(R), 5(R)-dihydroxyheptanamide, compound of formula (II):

Melting point: 76° C.

NMR ($CDCl_3$, delta scale): 6.10 (NH), 5.98 ($C_4$,-H), 5.79 ($C_3$,-H), 5.2 ($C_5$,-H), 5.42 ($C_8$,-H), 4.76 (OH), 4.20 ($C_3$-H), 3.80 ($C_5$-H), 3.62 (OH) and 3.25 ($C_1$,-H).

Mass spectrum: m/e 477 (M$^+$) with major fragments at m/e 459, 441, 375, 360, 339, 342, 251, 199, 173 and 159.

Infra red spectrum (KBr): principal peaks at wave numbers ($cm^{-1}$) 3200–3520 (OH and NH), 2885–3030 (C—H), 1730 (ester C=O), 1635 (amide C=O), 1605 (amide C=O) and 1185 (ester C—O—C).

Example 3

Example 3=N-butyl-7-[1(S), 2(S), 6(R), 7,8(S), 8a(R)-hexahydro-2,6-dimethyl-8-[[2(S)-methylbutanoyl]oxy]-1-naphthyl]-3(R), 5(R)-bis[(tetrahydropyranyl)oxy]heptanamide, compound of formula (III):

Melting point: 131°–133° C.

$[\alpha]_D$ (5 mg/ml acetonitrile) +286°

NMR (CDCL$_3$, delta scale): 5.99 (C$_5$-H), 5.79 (C$_6$-H), 5.51 (C$_4$-H), 5.37 (C$_1$-H), 4.63 (C$_{2'}$-H) and 4.36 (C$_{4'}$-H).

Mass spectrum: m/e 418 (M$^+$) with major fragments at m/e 302, 284, 199, 173 and 159.

Infra red spectrum (KRr): principal peaks at wave numbers (cm$^{-1}$) 3545 (OH), 2850–3050 (C—H), 1715 (ester C═O), 1700 (amide C═O), 1275 (lactone C—O—C) and 1170 (ester C—O—C).

Example 4

Example 4=N-butyl-7-[1(S), 2(S), 6(R), 7,8(S), 8a(R)-hexahydro-2,6-dimethyl-8-[[2,2-dimethylbutanoyl]oxy]-1-naphthyl]-3(R), 5(R)-bis[(tetrahydropyranyl)oxy]heptanamide, compound of formula (IV):

NMR (CDCL$_3$, delta scale): 6.95, 6.81, 6.42, 6.26 (NH), 5.98 (C$_{4'}$-H), 5.78 (C$_{3'}$-H), 5.49 (C$_{5'}$-H), and 5.33 (C$_{8'}$-H).

Infra red spectrum (NaCl): principal peaks at wave numbers (cm$^{-1}$) 3365 (NH), 2878–3030 (C—H), 1730 (ester C═O) and 1662 (amide C═O).

Example 5

Example 5=N-butyl-7-[1(S), 2(S), 6(R), 7,8(S), 8a(R)-hexahydro-2,6-dimethyl-8-[[2,2-dimethylbutanoyl]oxy]-1-naphthyl]-3(R), 5(R)-dishydroxyheptanamide, compound of formula (V) example 1d:

NMR (CDCL$_3$, delta scale): 6.42 (NH), 5.98 (C$_{4'}$-H), 5.78 (C$_{3'}$-H), 5.50 (C$_{5'}$-H), 5.42 (C$_{8'}$-H), 4.81 (OH), 4.19 (C$_3$-H), 3.79 (C$_5$-H), 3.74 (OH) and 3.25 (C$_1$-H).

Mass spectrum: m/e 477 (M$^+$) with major fragments at m/e 459, 441, 375, 360, 339, 342, 251, 199, 173 and 159.

Infra red spectrum (NaCl): principal peaks at wave numbers (cm$^{-1}$) 3220–3520 (OH and NH), 2885–3030 (C—H), 1720 (ester C═O), 1645 (amide C═O), 1560 (amide C═O) and 1160 (ester C—O—C).

Example 6

Preparation of lovastatin ethylamide acetonide: N-ethyl-7-[1(S), 2(S), 6(R), 7,8(S), 8a(R)-hexahydro-2,6-dimethyl-8-[[2(S)-methylbutanoyl]oxy]-1-naphthyl]-3(R), 5(R)-O-isopropylideen]heptanamide, compound of formula (VII) (wherein R$^1$ is methyl, R$^2$ is ethyl and R$^5$=R$^6$ is methyl).

To a solution of lovastatin ethylamide of the Example 1a (3.0 g, 6.7 mmol) in 2,2-dimethoxypropane (20 ml), 210 mg para-toluenesulfonic acid monohydrate (210 mg, 1.1 mmol) was added. The solution was stirred at 20° C.–25° C. for 30 minutes. Then ethyl acetate (10 ml) and 5% m/V aqueous sodiumbicarbonate (20 ml) was added. The mixture was stirred vigorously and the layers were allowed to separate. The organic layer was washed successively with 5% m/V aqueous sodiumbicarbonate (20 ml) and brine (20 ml). The organic layer was dried over sodiumsulfate, filtered and evaporated to dryness under reduced pressure to obtain a yellow coloured oil. For characterization purposes, an aliquot was crystallized from n-hexane to obtain an off white solid.

NMR (CDCL$_3$, delta scale): 6.26 (NH), 5.99 (C$_{4'}$-H), 5.78 (C$_{3'}$-H), 5.51 (C$_{5'}$-H), 5.34 (C$_{8'}$-H), 1.44, 1.38 (O—C(CH$_3$)—CH$_3$).

Infra red spectrum (KBr): principal peaks at wave numbers (cm$^{-1}$) 3300 (NH), 2870–3010 (C—H), 1720 (ester C═O), 1657 (amide C═O), 1542 (amide C═O).

Melting point: 90–91° C.

Example 7

Preparation of simvastatin ethylamide acetonide: N-ethyl-7-[1(S), 2(S), 6(R), 7,8(S), 8a(R)-hexahydro-2,6-dimethyl-8-[[2,2-dimethylbutanoyl]oxy]-1-naphthyl]-3(R), 5(R)-O-isopropylideen]heptanamide, compound of formula (VIII) (wherein R$^1$ is methyl, R$^2$ is ethyl and R$^4$ is methyl and R$^5$=R$^6$=R$^7$ is methyl).

n-Butyllithium in hexane (30 ml, 0.048 mol) was added to a stirred solution of pyrrolidine (4.0 ml 0.048 mol) in anhydrous tetrahydrofuran (15 ml) at −20° C. under an inert atmosphere of nitrogen. The mixture was stirred at −20° C. for 30 minutes and then added dropwise to a stirred solution of lovastatin ethylamide acetonide of the example 6 (10.0 g, 0.021 mol) in tetrahydrofuran (50 ml) cooled to −35° C., in such a rate as to keep the temperature between −30° C. and −35° C. After completion of the addition the mixture was stirred at −35° C. for 2 hours. Then methyliodide (2.0 ml, 0.032 mol) was added in one portion. After an initial 15° C. exotherm, the solution was recooled to −30° C. and maintained for an additional 30 minutes. The mixture was then quenched by addition of water (80 ml) and allowed to warm to ~5° C., while stirring. The phases were separated and the aqueous layer was extracted with ethyl acetate (2×50 ml). The combined organic layers were extracted with 1N aqueous hydrochloric acid (100 ml). The resulting organic phase was concentrated at reduced pressure to obtain an orange coloured oil.

NMR (CDCL$_3$, delta scale): 6.28 (NH), 5.98 (C$_{4'}$-H), 5.77 (C$_{3'}$-H), 5.50 (C$_{5'}$-H), 5.32 (C$_{8'}$-H), 1.44, 1.38 (O—C(CH$_3$)—CH$_3$).

Infra red spectrum (NaCl): principal peaks at wave numbers (cm$^{-1}$) 3310 (NH), 2894–3017 (C—H), 1718 (ester C═O), 1651 (amide C═O), 1547 (amide C═O).

Example 8

Preparation of simvastatin ethylamide acetonide: N-ethyl-7-[1(S), 2(S), 6(R), 7,8(S), 8a(R)-hexahydro-2,6-dimethyl-8-[[2,2-dimethylbutanoyl]oxy]-1-naphthyl]-3(R), 5(R)-dihydroxyheptanamide, compound of formula (V) (wherein R$^1$ is methyl, R$^2$ is ethyl and R$^7$ is methyl).

Methanol (50 ml) was added to the crude simvastatin-ethylamide acetonide (10.3 g). Then water (4 ml) and methanesulfonic acid (125 ml) was added and the resulting solution was stirred for 6 hours at 30° C. For characterization purpose, an aliquot was evaporated, dissolved in ethyl acetate and extracted with an aqueous solution of sodium bicarbonate, water, dried over sodium sulfate, filtrated and evaporated to dryness to obtain an orange coloured oil.

Identification data of the compound were identical with those of example 1d, step i.

The entire disclosure set forth in each of the U.S. patents mentioned above is expressly incorporated herein by reference. Further, the entire disclosure of application number 1008502 filed in The Netherlands on Mar. 5, 1998 and from which a right of priority is claimed is also incorporated by reference herein.

The above discussion of this invention is directed primarily to preferred embodiments and practices thereof. It will be readily apparent to those skilled in the art that further changes and modifications in actual implementation of the concepts described herein can easily be made or may be learned by practice of the invention, without departing from the spirit and scope of the invention as defined by the following claims.

We claim:

1. A process, which comprises reacting a compound of formula (II):

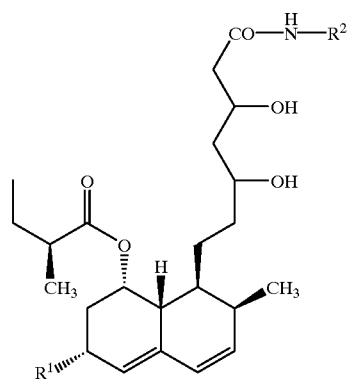

(II)

wherein $R^1$ represents hydrogen or methyl and $R^2$ represents methyl or ethyl; with a protecting agent to form a compound of formula (III):

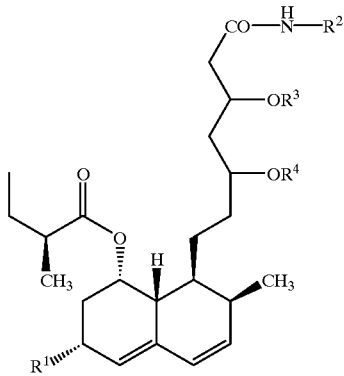

(III)

wherein $R^1$ and $R^2$ are as defined above in formula (II) and $R^3$ and $R^4$ each independently represent an alkyl group, an ether group, a thioether group, an aryl group, an aralkyl group, an alkenyl group, a cyclic ether group, or a cyclic thioether group.

2. The process according to claim 1, wherein $R^3$ and $R^4$ represent a cyclic ether group or a cyclic thioether group.

3. The process according to claim 2, wherein $R^3$ and $R^4$ are selected from the group consisting of a tetrahydropyranyl, an alkoxytetrahydropyranyl, a tetrahydrothiopyranyl, a dioxanyl, and tetrahydrofuranyl.

4. The process according to claim 1, wherein $R^3$ and $R^4$ represent an alkyl group, an ether group, a thioether group, an aryl group or an aralkyl group.

5. The process according to claim 4, wherein $R^3$ and $R^4$ represent an alkyl group.

6. The process according to claim 1, wherein $R^3$ and $R^4$ are selected from the group consisting of methyl, methoxymethyl, methylthiomethyl, benzyloxymethyl, t-butoxymethyl, 2-methoxyethoxymethyl, 1-ethoxyethyl, t-butyl, allyl, benzyl, tetrahydropyran-2-yl, tetrahydrothiopyran-2-yl, 4-methoxytetrahydropyran-2-yl, 1,4-dioxan-2-yl and tetrahydrofuran-2-yl.

7. The process according to claim 1, wherein $R^2$ is ethyl.

8. The process according to claim 1, wherein said protecting agent is a dihyhropyran compound and $R^3$ and $R^4$ both represent the same tetrahydropyranyl group.

9. The process according to claim 1, which further comprises alkylating said formed compound of formula (III) to form a compound of formula (IV), respectively:

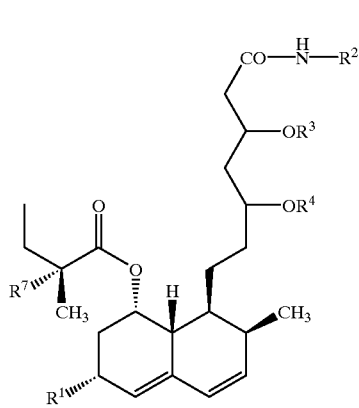

(IV)

wherein $R^7$ represents methyl or ethyl.

10. The process according to claim 9, wherein said alkylating is carried out by subjecting said compound of formula (III) to a compound of the formula $R^7$-X, wherein X is chlorine, bromine or iodine, in the presence of a base.

11. The process according to claim 9, which further comprises deprotecting said alkylated compound of formula (IV) to form a compound of formula (V):

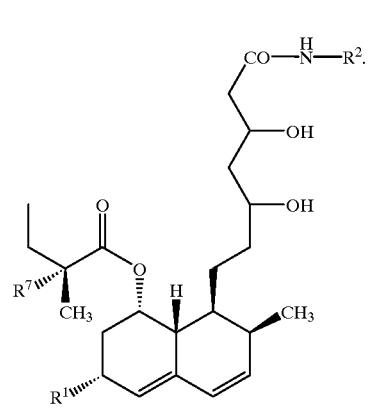

(V)

12. The process according to claim 11, wherein said deprotection is carried out by hydrolyzing the protecting groups in an acidic medium.

13. The process according to claim 11, which further comprises hydrolysis of the amide moiety of the compound of formula (V) and relactonization to produce a compound of formula (VI):

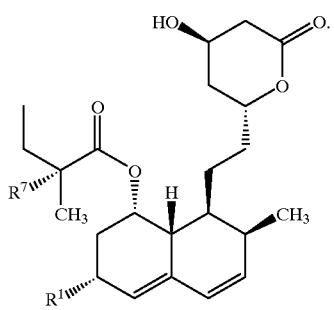

(VI)

14. The process according to claim 13, wherein $R^7$ is methyl and $R^1$ is methyl.

15. The process according to claim 1, which further comprises reacting a compound of formula (I):

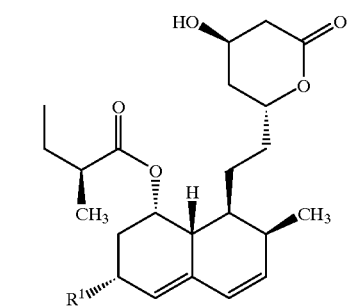

(I)

with an amine of the general formula $R^2NH_2$ to produce said compound of formula (II).

16. A process which comprises:

(a) reacting a compound of formula (I) with an amine compound of the formula $R^2NH_2$ to form a compound of formula (II):

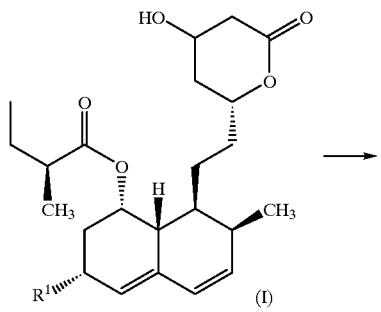

(I)

-continued

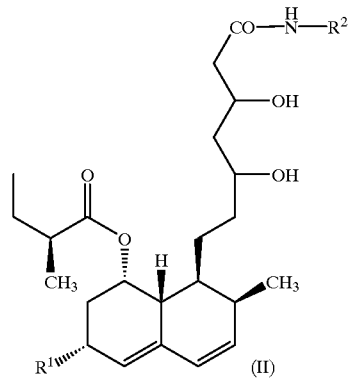

(II)

wherein $R^1$ represents hydrogen or methyl and $R^2$ represents methyl or ethyl;

(b) reacting said compound of formula (II) with a protecting agent to form a compound of formula (III):

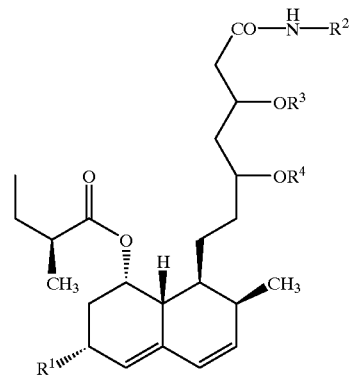

(III)

wherein $R^3$ and $R^4$ are the same and each represents a tetrahydropyranyl group, a tetrahydrofuranyl group or a dioxanyl group;

(c) alkylating said compound of formula (III) formed in said step (b) by treating with an alkali metal amide and methyliodide to form a compound of formula (IV):

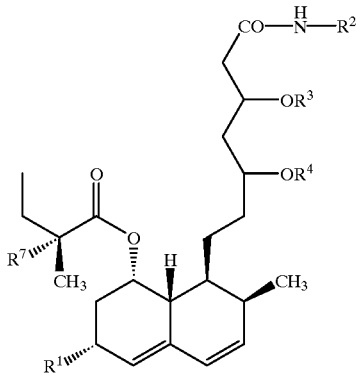

(IV)

wherein $R^7$ is methyl;

(d) deprotecting said compound of formula (IV) produced in step (c) by acidic hydrolysis to form a compound of formula (V):

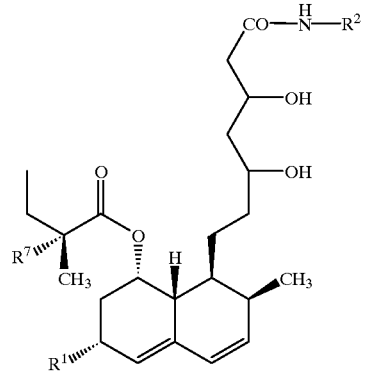

and (e) hydrolyzing the amidic moiety of said compound of formula (V) and relactonizing to obtain a compound of formula (Vl):

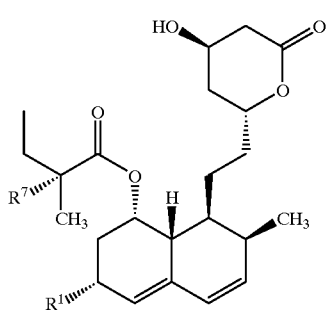

17. A compound of formula (III) or (IV):

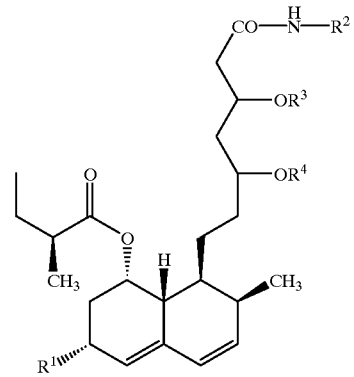

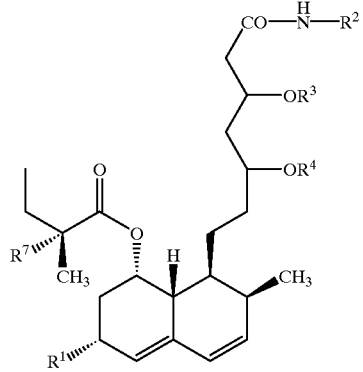

wherein $R^1$ is hydrogen or methyl; $R^2$ represents methyl or ethyl; $R^3$ and $R^4$ each independently represent an alkyl group, an ether group, a thioether group, an aryl group, an aralkyl group, an alkenyl group, a cyclic ether group, or a cyclic thioether group; and $R^7$ represents methyl or ethyl.

18. The compound according to claim 17, wherein said compound is selected from the group consisting of:

lovastatin ethylamide bis-tetrahydropyran-2-ylether; and

Simvastatin ethylamide bis-tetrahydropyran-2-ylether.

19. A compound of the formula (V):

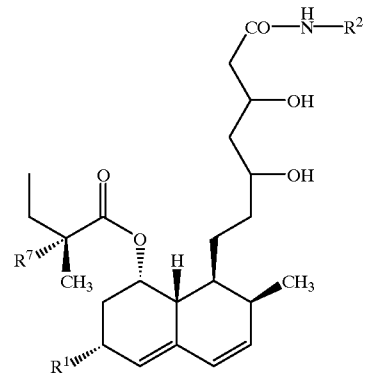

wherein $R^1$ represents hydrogen or methyl, $R^2$ represents methyl or ethyl, and $R^7$ represents methyl or ethyl.

* * * * *